US006969197B2

(12) United States Patent
Sedley

(10) Patent No.: US 6,969,197 B2
(45) Date of Patent: Nov. 29, 2005

(54) STERILIZABLE PACKAGE

(75) Inventor: Ronald Sedley, Boca Raton, FL (US)

(73) Assignee: Ronpak, Inc., South Plainfield, NJ (US)

( * ) Notice: Subject to any disclaimer, the term of this patent is extended or adjusted under 35 U.S.C. 154(b) by 348 days.

(21) Appl. No.: 10/116,810

(22) Filed: Apr. 5, 2002

(65) Prior Publication Data

US 2003/0188981 A1 Oct. 9, 2003

(51) Int. Cl.[7] .............................................. B65D 81/18
(52) U.S. Cl. ...................... 383/200; 206/438; 206/439; 206/484.1; 383/209
(58) Field of Search ............................... 206/363, 364, 206/438, 439, 824, 264, 484.1; 383/200–209

(56) References Cited

U.S. PATENT DOCUMENTS

| 1,948,593 | A | * | 2/1934 | Patterson | 206/264 |
|---|---|---|---|---|---|
| 2,008,361 | A | * | 7/1935 | Lindsey | 229/87.05 |
| 2,079,328 | A | * | 5/1937 | McBean | 229/87.05 |
| 3,070,225 | A | * | 12/1962 | Schwartz | 206/438 |
| 3,086,647 | A | | 4/1963 | Krezanoski | 206/56 |
| 3,146,912 | A | | 9/1964 | Twersky | 222/107 |
| 3,186,628 | A | * | 6/1965 | Rohde | 383/209 |
| 3,189,174 | A | | 6/1965 | Cormack | 206/63.2 |
| 3,227,359 | A | * | 1/1966 | Hanlon | 383/207 |
| 3,315,802 | A | * | 4/1967 | Lonholdt et al. | 206/205 |
| 3,334,804 | A | | 8/1967 | Watts, Jr. | 229/53 |
| 3,399,760 | A | | 9/1968 | Hechler, IV | |
| 3,410,393 | A | * | 11/1968 | Lee | 206/363 |
| 3,419,137 | A | * | 12/1968 | Walck, III | 206/364 |
| 3,642,126 | A | | 2/1972 | Kurtz et al. | 206/63.3 |
| 3,704,096 | A | * | 11/1972 | Verses | 436/1 |
| 3,724,651 | A | * | 4/1973 | Link | 206/363 |
| 3,768,725 | A | | 10/1973 | Pilaro | 229/66 |
| 3,930,580 | A | * | 1/1976 | Bazell et al. | 206/439 |
| 4,176,746 | A | * | 12/1979 | Kooi | 206/438 |
| 4,190,154 | A | * | 2/1980 | Clark | 206/438 |
| 4,194,622 | A | * | 3/1980 | Lewis | 206/363 |
| 4,781,297 | A | * | 11/1988 | Abrahamsson et al. | 383/201 |
| 4,826,009 | A | * | 5/1989 | Young | 206/440 |
| 5,613,779 | A | | 3/1997 | Niwa | 383/201 |
| 5,655,653 | A | * | 8/1997 | Chester | 206/63.5 |

* cited by examiner

Primary Examiner—Jim Foster
(74) Attorney, Agent, or Firm—Darby & Darby

(57) ABSTRACT

A sterilizable package is formed of a first sheet connected to a second sheet. The first sheet forms a first side of the package and a portion of the second side of the package. The second sheet is connected to the first sheet to define an interior chamber of the package. The second sheet forms a portion of the second side of the package. The second sheet has a first edge. A plurality of slots are disposed along the first edge at predetermined spaced apart locations. The first sheet is folded over along a fold line, thereby forming a folded portion. The folded portion is connected to the second sheet. The folded portion forms a portion of the second side of the package. The fold line forms a first edge of the package. The first edge of the second sheet is in the interior of the package between the first side and the folded portion of the first sheet.

21 Claims, 9 Drawing Sheets

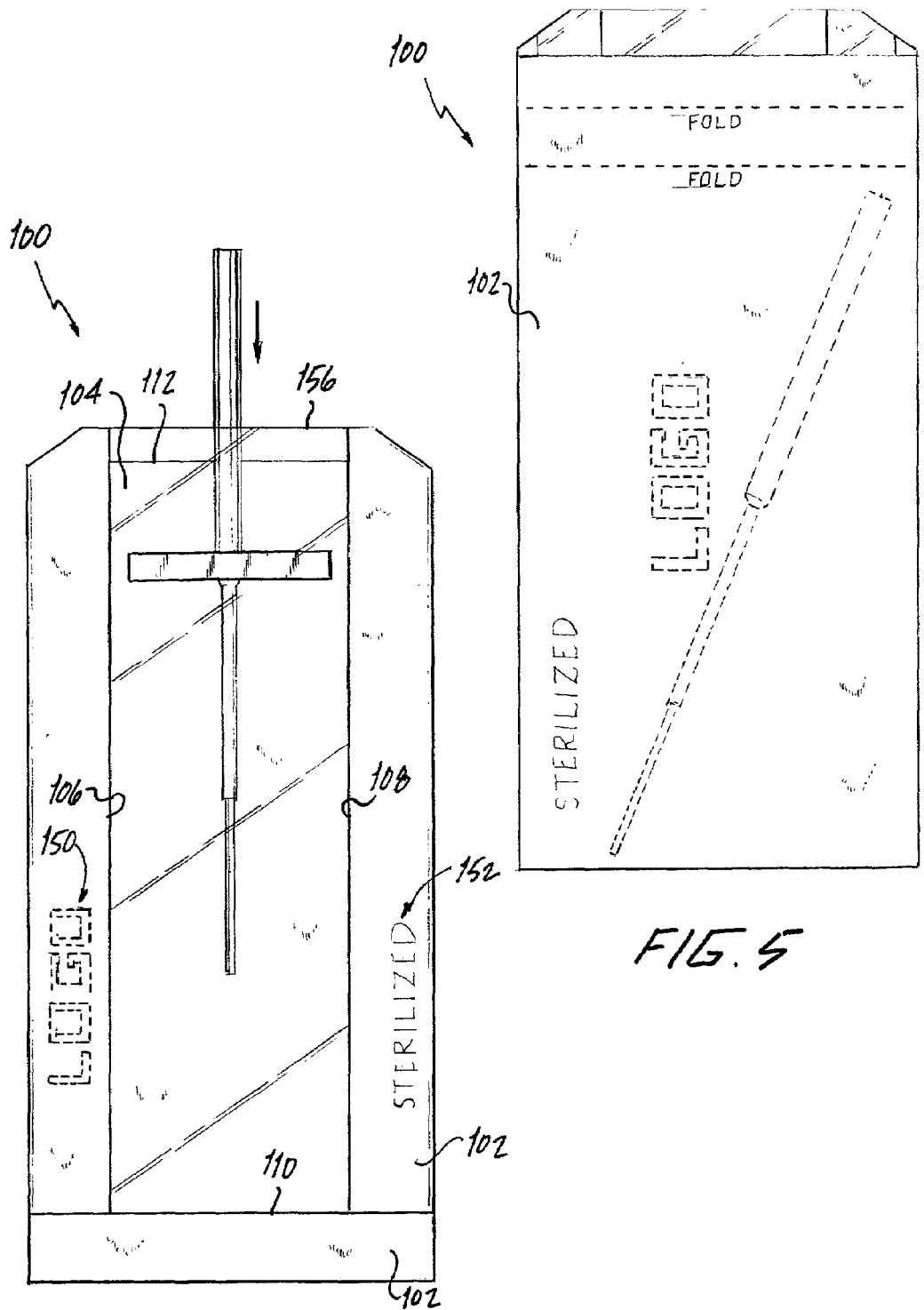

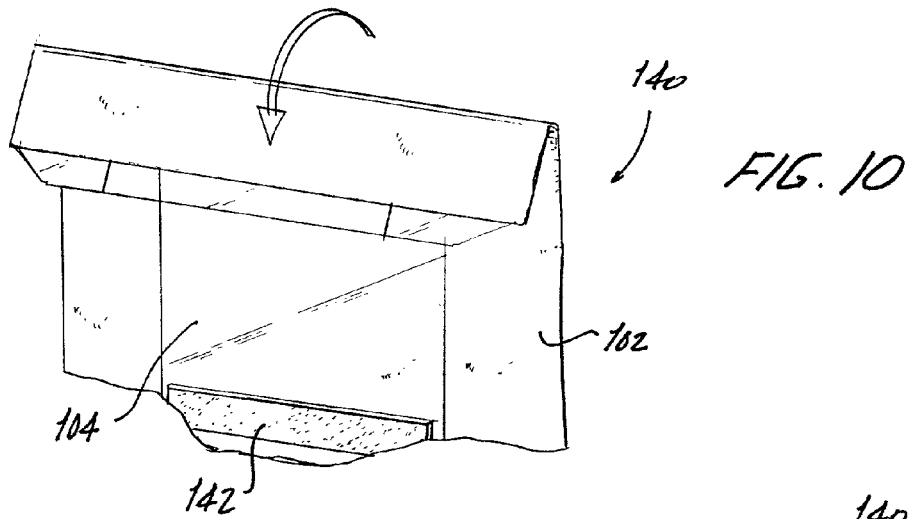
FIG. 10
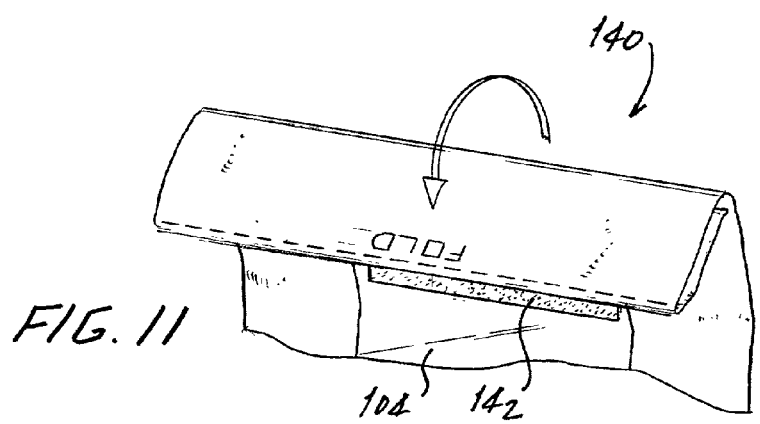
FIG. 11
FIG. 12
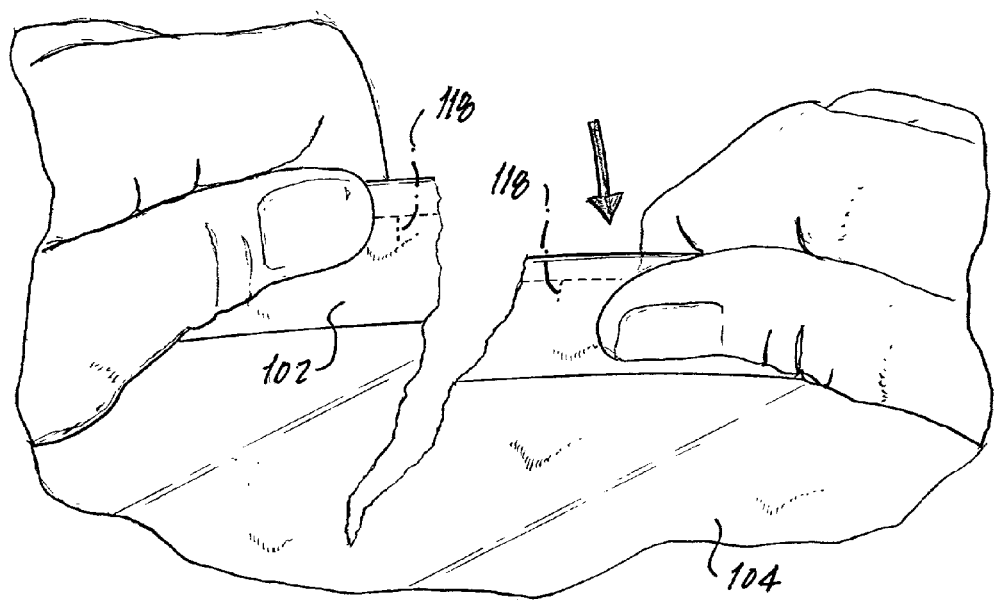

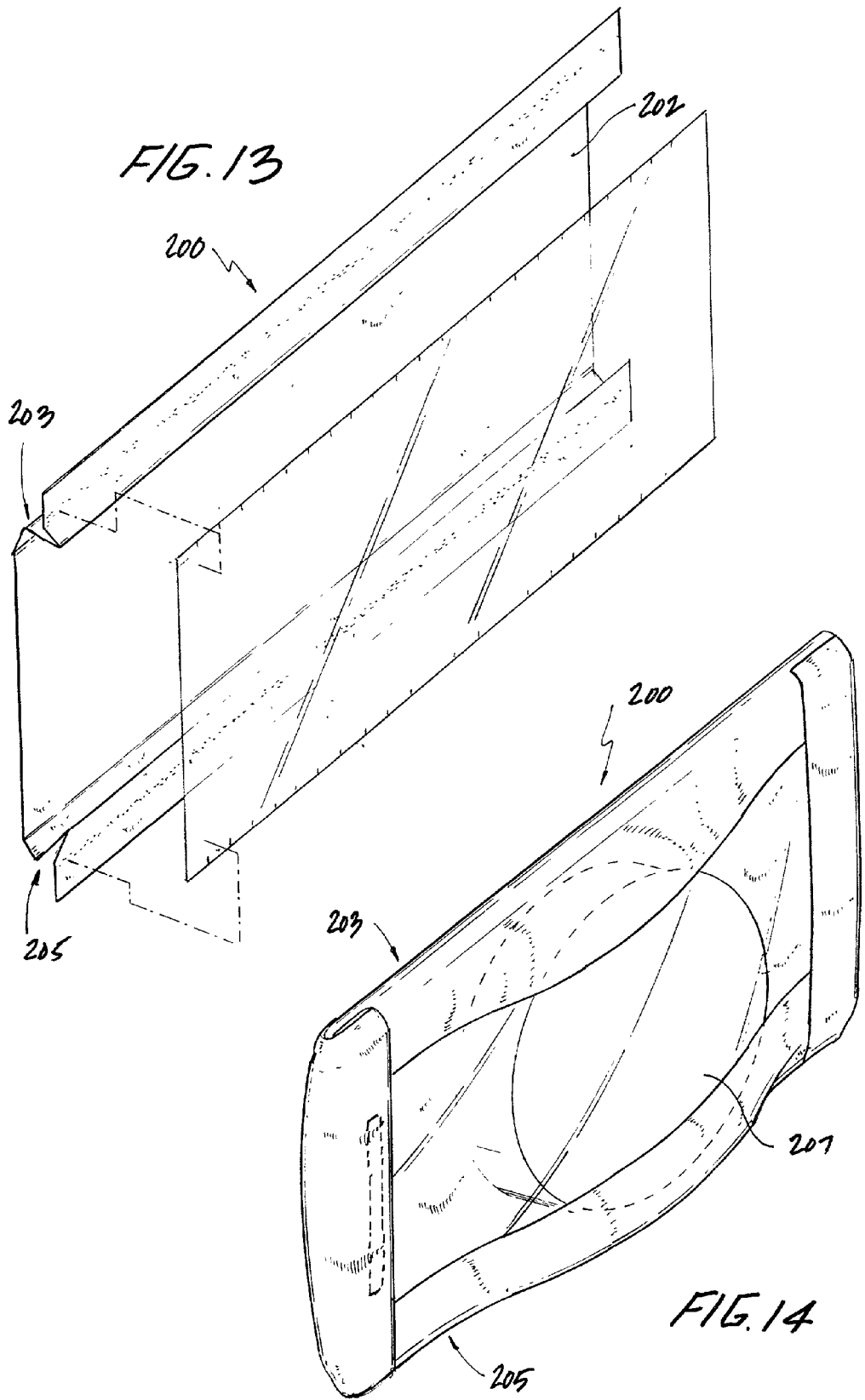

STERILIZABLE PACKAGE

BACKGROUND OF THE INVENTION

1. Field of the Invention

The present invention relates to a sterilizable package. More specifically, the present invention relates to a sterilizable package that can be torn open from any where across the side of the bag as desired by the user.

2. Discussion of the Related Art

Packages for the reception and, thereafter, sterilization of medical products and the like are known in the art. One example of such a package is shown in FIGS. 1–3, where a prior art sterilizable package 10 is illustrated. Package 10 is formed of a ply 12. Ply 12 itself is formed of two (2) of plies of plastic material. One of the two plies is a carrier and the other ply is a heat sealer, to effect the heat seal between these two plies. For example, one ply is conventionally made of polyester and the other ply is conventionally made of polypropylene. A specially treated paper 14 is disposed opposite to ply 12, which is known in the art as a sterilizable kraft paper. Ply 12 is heat sealed to paper 14 along a heat seal line 16 along essentially three edges of the package. To use package 10, the product to be sterilized is inserted into the open top of the package, as illustrated in FIG. 1. Thereafter, a backing paper 18 is removed to expose an adhesive 20 so that the top open edge of package 10 can be closed by applying adhesive 20 to ply 14. Thereafter, package 10 is sterilized by any conventional sterilizing technique so that the product may then be stored until the product is required for use. To open the sterilized package 10 and access the product, the user will grasp a bottom end 22 of package 10 and separate ply 12 from ply 14, as illustrated in FIG. 3. This process usually requires a certain amount of deftness by the user and involves the risk that the sterilized product may accidentally fall out from package 10. In addition, because this package utilizes two plies of film and a heat seal between the film and the paper, it is very difficult to provide gussets in the side of the bag to increase the volume for receiving the product to be sterilized because this would effectively double the side wall thickness in the gusset area immediately adjacent to where the heat seal is formed.

U.S. Pat. No. 3,642,126 to Kurtz et al. discloses another package for receiving medical products. The package includes a sealed compartment 3 for containing a medical object 4. An edge 8 of the package is provided with a plurality of tear-initiating areas 9. These areas are illustrated as being slots that extend through the front and back sheets 1, 2 from the outer edge of the package towards the sealed compartment 3. A second opposite edge is provided with the same tear-initiating areas 9. To open the package, one grabs the package near one of the tear-initiating areas and the user tears open the package from this edge 8. Thus, the package in accordance with the Kurtz disclosure has the slots 9 extending all the way to the outer edge of the package. With this structure there is a significant risk that the package could be accidentally snagged and thereby inadvertently opened. In addition, having the slits at the edge of the package does not provide an orderly package for storing or stacking purposes.

Accordingly, there is a need in the art for a sterilizable package that can be easily torn open from anywhere along the side of the package, with minimal risk of the package being inadvertently opened. In addition, there is a need to provide a sterilizable package that can accommodate relatively larger volume products.

SUMMARY OF THE INVENTION

In accordance with a currently preferred exemplary embodiment of the present invention, a sterilizable package formed of a first sheet connected to a second sheet achieves these and other needs. More specifically, the first sheet forms a first side of the package and a portion of the second side of the package. The second sheet is connected to the first sheet to define an interior chamber of the package. The second sheet forms a portion of the second side of the package. The second sheet has a first edge. A plurality of slots are disposed along the first edge at predetermined spaced apart locations. The first sheet is folded over along a fold line, thereby forming a folded portion. The folded portion is connected to the second sheet. The folded portion forms a portion of the second side of the package. The fold line forms a first edge of the package. The first edge of the second sheet is in the interior of the package between the first side and the folded portion of the first sheet.

BRIEF DESCRIPTION OF THE DRAWING FIGURES

The above and still further objects, features and advantages of the present invention will become apparent upon consideration of the following detailed description of a specific embodiment therefor, especially when taken in conjunction with the accompanying drawings wherein the reference figures are utilized to designate like components, and wherein:

FIG. 4 is a plan view of a sterilizable package in accordance with the present invention;

FIG. 5 is a plan view of a sterilizable package of FIG. 4, shown with a medical product being disposed therein;

FIG. 10 is a partial perspective view of the bottom portion of the sterilizable package, shown being folded into a sealed position;

FIG. 11 is a partial perspective view of the bottom portion of the sterilizable package in accordance with the present invention, shown in a further step of being folded into the sealed position;

FIG. 12 is a partial perspective view of a side of the sterilizable package in accordance with the present invention, shown being torn to access the sterilized contents of the package;

FIG. 13 is a perspective exploded view of the first and second sheet of a gusseted sterilizable package in accordance with the present invention; and FIG. 14 is a perspective view of a gusseted sterilizable package shown with a product therein.

DETAILED DESCRIPTION OF THE PREFERRED EMBODIMENT

Figure 1:
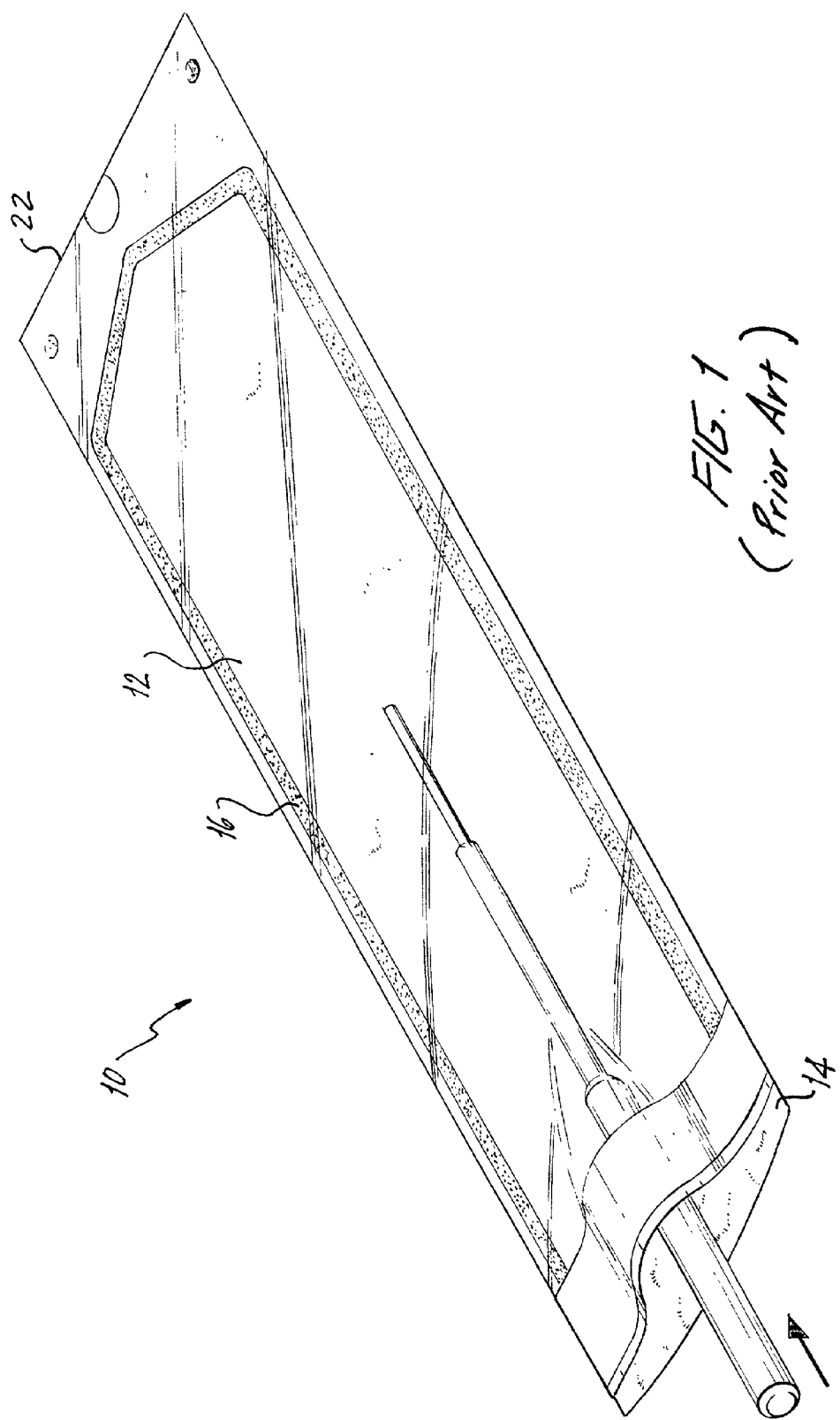
FIG. 1 is a perspective view of a sterilizable package in accordance with the prior art.
Figure 2:
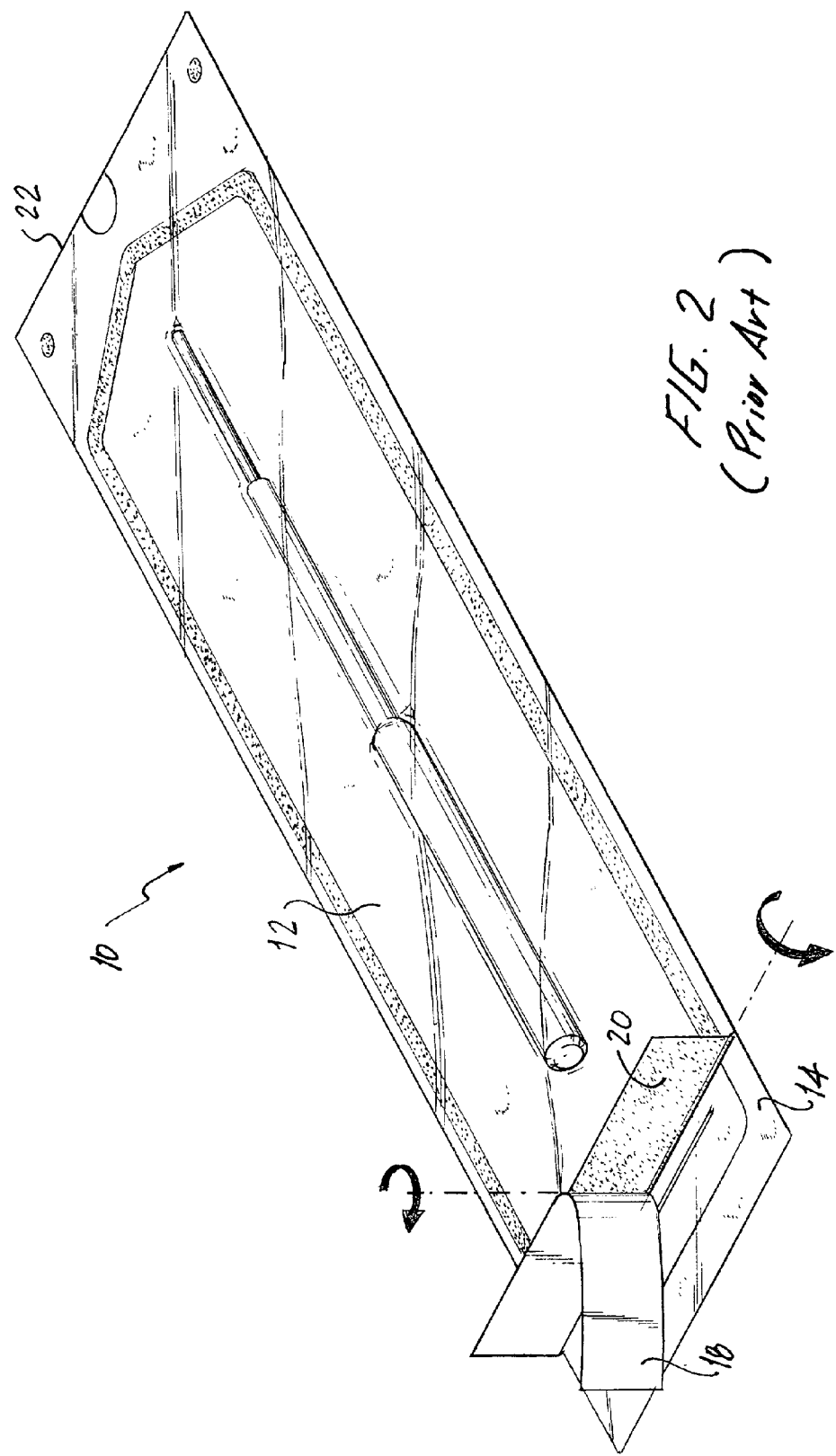
FIG. 2 is a perspective view of the sterilizable package of FIG. 1, shown with a medical product being sealed therein.
Figure 3:
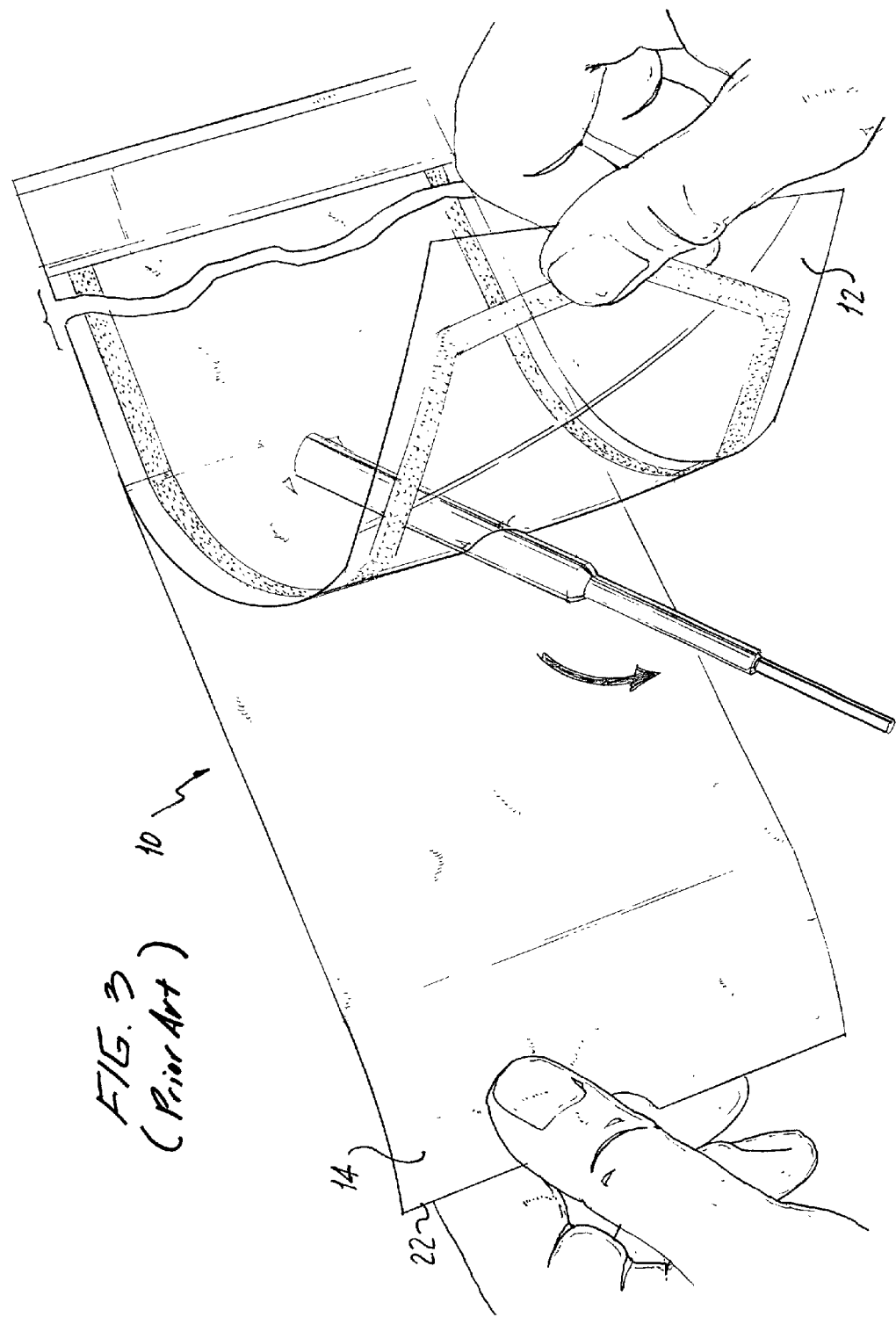
FIG. 3 is a perspective view of the sterilizable package of FIG. 1, shown in the process of being opened.
Figure 6:
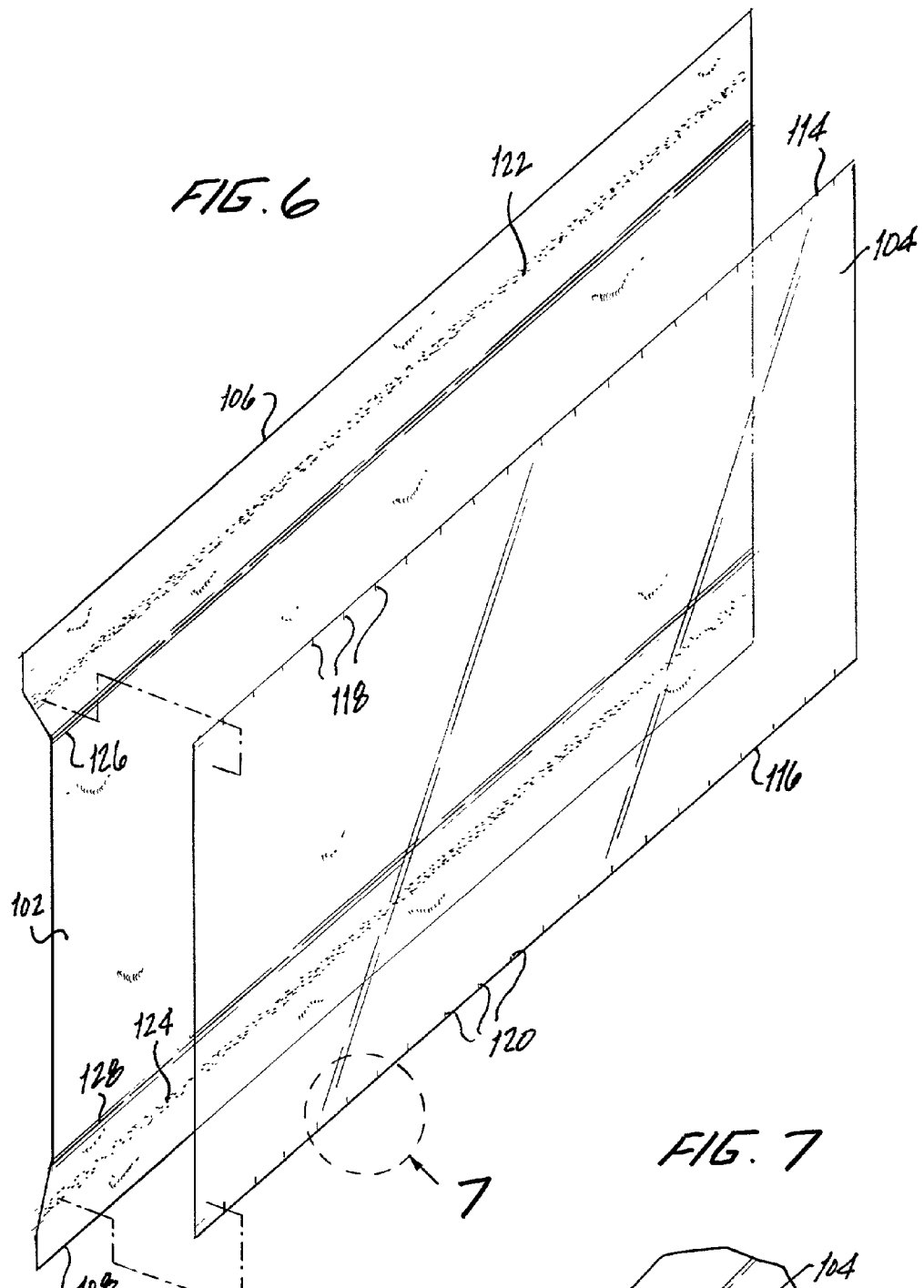
FIG. 6 is a partial exploded perspective view of the first sheet and second sheet of the sterilizable package in accordance with the present invention.
Figure 7:
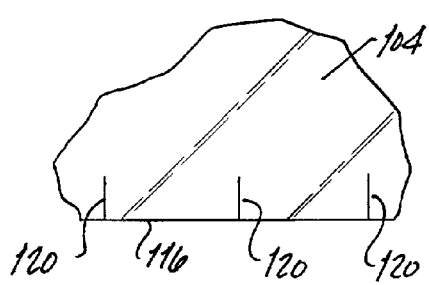
FIG. 7 is an enlarged detail of circle 7 from FIG. 6.

Referring now to FIGS. 4–12, a sterilizable package 100 in accordance with the present invention is illustrated. Sterilizable package 100 is formed of a first sheet 102 and a second sheet 104. First sheet 102 has a first edge 106, a second edge 108, a third edge 110 and a fourth edge 112. The second sheet 104 has a first edge 114 and a second edge 116. A plurality of slots 118 are disposed along first edge 114 at predetermined spaced apart locations, preferably along the entire length of edge 114. A second set of a plurality of slots 120 are disposed along the second edge 116, again at predetermined spaced apart locations, preferably along the entire length of edge 116.

Figure 8:
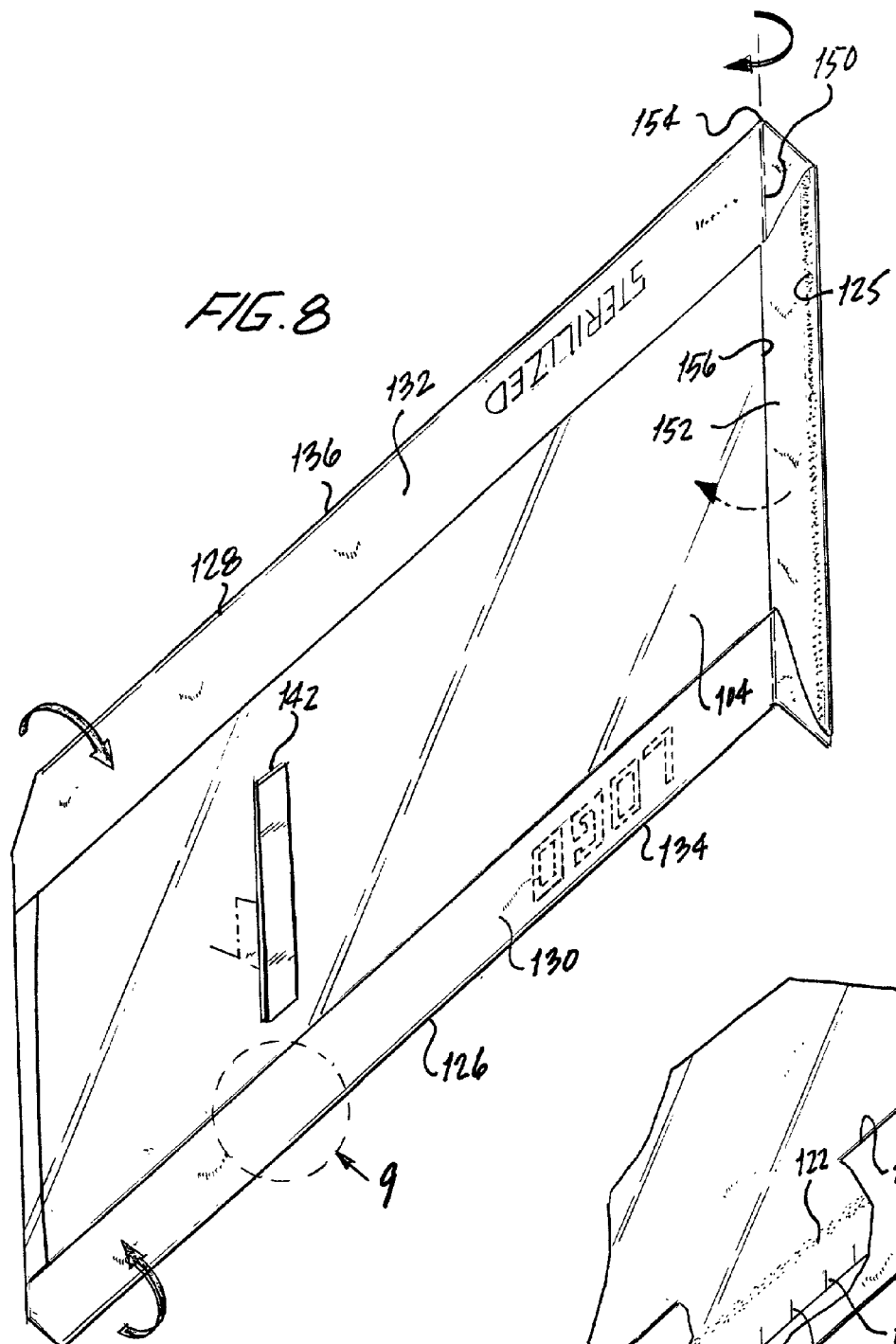
FIG. 8 is a perspective view of the first and second sheet of the sterilizable package in accordance with the present invention, showing how the first sheet is attached to the second sheet.
Figure 9:
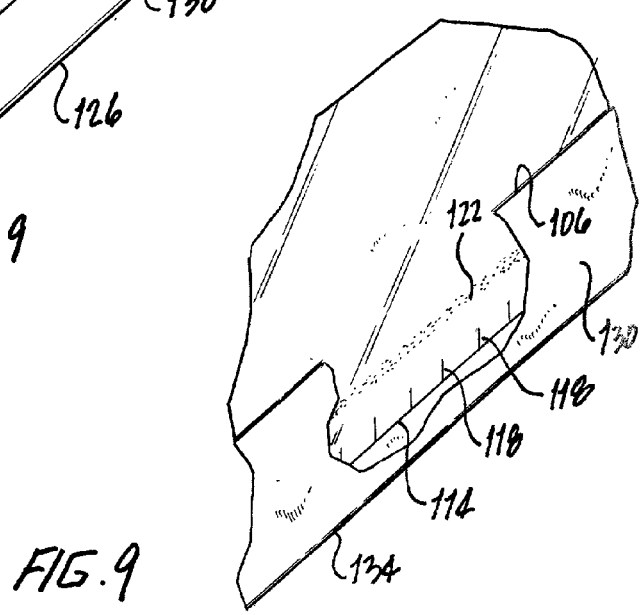
FIG. 9 is an enlarged detail of circle 9 from FIG. 8.
Figure 15:
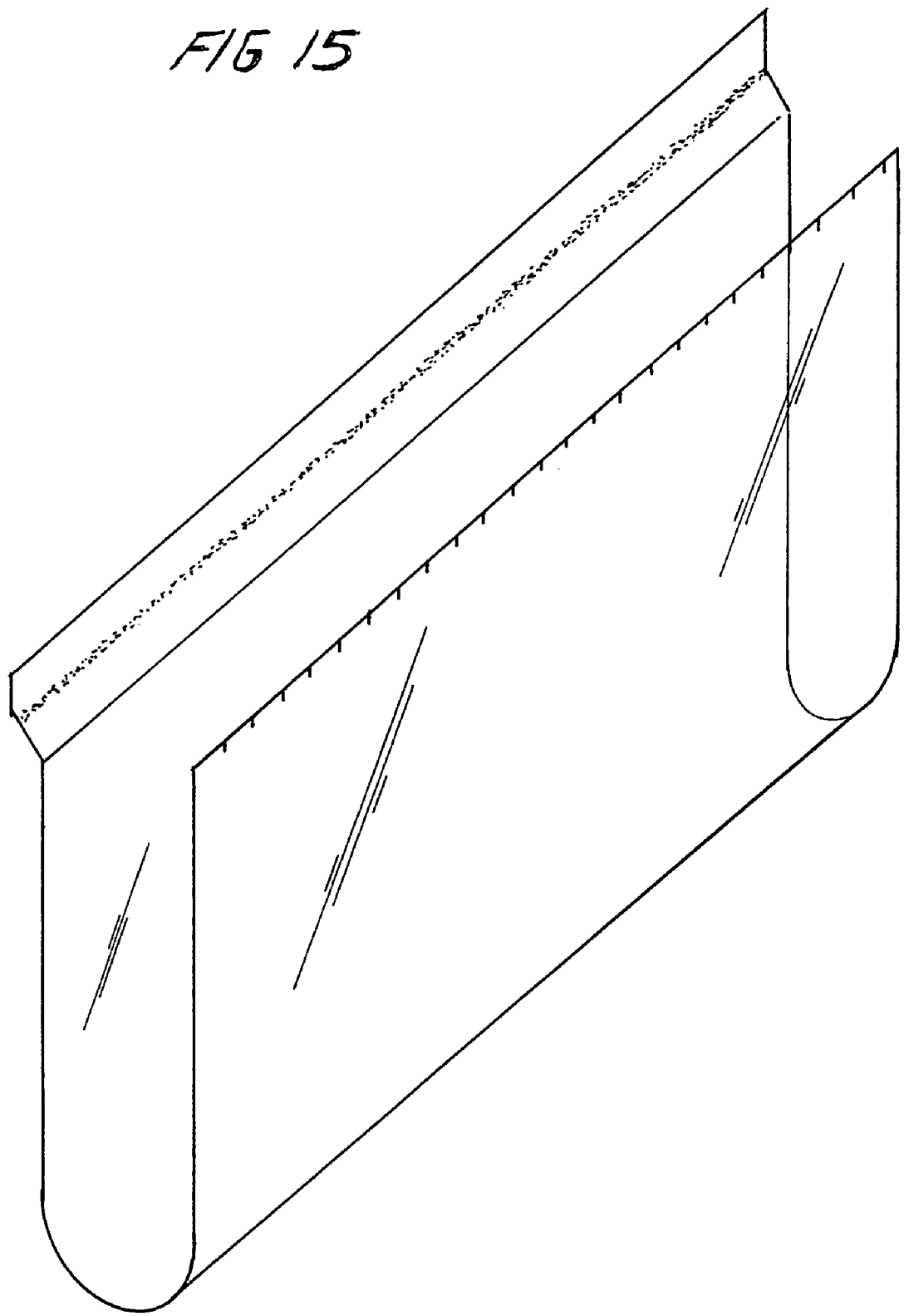

Referring now to FIGS. 6–9, to attach first sheet 102 to second sheet 104, an adhesive is applied along a first glue line 122 and a second glue line 124. Thereafter, first sheet 102 is folded along a fold line 126, 128 thereby forming a folded over portion 130, 132. Fold line 126 forms a new first edge 134 of the package 100 and fold line 128 forms a new second edge 136 of the package 100. As illustrated in FIG. 9, first edge 114 of second sheet 104 is in the interior of the package between the first side of the package and the first folded portion 130 of first sheet 102. Additionally, as illustrated in FIG. 9, first edge 114 of the second sheet 104 is spaced inwardly from the first edge 134 of package 100. Also, as is clearly illustrated in FIG. 9, slots 118 are disposed outside of the glue line 122 so they do not impinge on the sterile area of the package.

Referring now to FIG. 8, first sheet 102 is folded over a third fold line 150 at a top portion of package 100. Thus, a third folded portion 152 is connected to second sheet 104 by a third glue line 125. Third folded portion 152 forms a portion of the second side of the package. Once folded and glued, third fold line 150 forms a third edge 154 of the package. A third edge 156 of second sheet 104 is disposed in the interior of the package between the first side of the package and the third folded portion 152 of first sheet 102. Third edge 156 of second sheet 104 preferably does not have any slots therein. However, third edge 156 and the fourth edge could have slots therein if desired by the user.

Referring now to FIGS. 10 and 11, the bottom portion of bag 100 is illustrated. As illustrated in FIGS. 4 and 5, a medical product or the like to be sterilized is first inserted into the package 100. Thereafter, the bottom portion of the package must be closed prior to sterilization. To achieve this an adhesive that is capable of withstanding sterilizing conditions is applied onto at least one of the two sheets 102, 104. As illustrated in FIGS. 10 and 11, the adhesive 142 is placed on sheet 104 and is of sufficient width to ensure a sterile sealing of the package during the sterilization process. A backing paper is preferably applied to the adhesive to protect the adhesive before it is required to be accessed to close the package, as is known in the art. The bottom of the package is preferably folded over at least twice before being sealed to the exposed adhesive 142. Thus, a tortuous path has been created to prevent germs or other bacteria from entering into the sealed, sterilized interior of the package. Once sealed, the package can be sterilized utilizing any conventional sterilizing condition, such as, for example, steam, dry heat, chemical vapor, ethylene oxide or radiation. Package 100 may now be stored until the product is required for use.

Referring now to FIG. 12, to open the sterilized package 100, the user may grab the package from anywhere on the side depending upon the size and location of the sterilized medical product contained within the bag. The bag may be torn partially or completely across depending upon the desires of the user. As illustrated in FIG. 12, the bag can be readily torn from the side due to the plurality of slits 118, 120 which aid in initiating the tear through sheets 102, 104. Once the bag has been torn sufficiently, the sterilized product can be accessed by the user for further use.

Second sheet 104 is preferably made of a transparent plastic film so that the user can readily identify the product contained within the sterilizable package. The plastic film must be made of a material that can withstand the sterilizing methods to be used. For example, if steam sterilizing is used, the plastic material must be able to withstand the relatively high temperatures of steam sterilization, which are conventionally around 136° C. Second sheet 104 may be made of films such as, for example, polypropylene, polyester film (e.g., MYLAR®, which is a biaxially oriented film), polycarbonate film or nylon.

First sheet 102 is preferably made of paper to permit the sterilant to pass into the interior and so that indicia, such as, for example, labels, and indicators, can be printed thereon. First sheet 102 must be made of a paper that can withstand the sterilizing methods to be used. Preferably, the paper is a bleached, kraft-type paper that is treated so that it will have a wet strength sufficient to withstand steam sterilization if this is the sterilization technique being used. Currently, a paper having a weight of 30–45 pounds per 3000 square yards is preferred.

The glue used to form glue lines 122, 124 must be made of an adhesive that is capable of withstanding the sterilizing methods to be used. In other words, the adhesive must not decompose or release from the film or the paper during the sterilization process. For example, polyurethane based adhesives and acrylic based adhesives are among those currently preferred for forming the glue lines.

The paper of the bag may be imprinted with a label 150 and a sterilization indicator 152, using techniques that are well known in the art. The sterilizer indicator will, for example, change with a readily observable change to indicate exposure to one or more given sterilization conditions. As illustrated in drawing FIGS. 4, 5 and 8, the word sterilized is used and typically the color of the word changes from one color to another when the packaging has been subject to a sterilization process. Additionally, the ink used to be applied to the bag must be of the type to withstand all sterilization conditions, without running. These types of inks are well known in the art.

Referring now to FIGS. 13 and 14, another gusseted sterilized package 200 in accordance with the present invention is illustrated. This embodiment is essentially similar to the embodiment of FIGS. 4–12 except that the sides of the paper sheet 202 are gusseted at 203, 205 to permit the package to expand to contain a product 207 having relatively greater width. All other aspects of the package 200 are similar to package 100 and will not be described in further detail for the sake of brevity in the disclosure.

The sterilizable package may also be formed from one sheet. For example, the first sheet will form the first side of the package and the second side of the package. The first sheet will have a first edge and a second edge. The first edge is then connected to the second edge thereby defining an interior chamber. A plurality of slots are disposed along the first edge at predetermined spaced apart locations. The first edge is in the interior of the package so that the slots will be within the interior of the package as well.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

What is claimed is:

1. A sterilizable package comprising:
    a first sheet forming a first side of the package and a portion of a second side of the package;
    a second sheet being connected to said first sheet thereby defining an interior chamber of the package, said second sheet forming a portion of the second side of the package, said second sheet having a first edge, a plurality of slots being deposed along said first edge at predetermined spaced apart locations;
    wherein said first sheet being folded over along a fold line forming a folded portion, said folded portion being connected to said second sheet, said folded portion forms a portion of the second side of the package, said fold line forming a first edge of said package, said first edge of said second sheet being in the interior of the package between the first side and the folded over portion of the first sheet.

2. The package according to claim 1, wherein said first edge of said second sheet is spaced inwardly from said first edge of said package.

3. The package according to claim 2, wherein said first sheet is glued to said second sheet along a glue line.

4. The package according to claim 3, wherein said plurality of slots are displaced between said glue line and said first edge of said package.

5. The packaging according to claim 1, wherein said second sheet is essentially transparent.

6. The package according to claim 1, wherein said first sheet is gusseted along said fold line.

7. The packaging according to claim 1, wherein said plurality of slots are disposed essentially along the entire first edge of said second sheet.

8. The packaging according to claim 1, wherein said entire second sheet forming a portion of the second side of the package.

9. The packaging according to claim 1, wherein said second sheet having a second edge, a second set of a plurality of slots being disposed along said second edge at predetermined spaced apart locations.

10. The packaging according to claim 9, wherein said first sheet being folded over along a second fold line forming a second folded portion, said second folded portion being connected to said second sheet, said second folded portion forms a portion of the second side of the package, said second fold line forming a second edge of said package, said second edge of said second sheet being in the interior of the package between the first side and the second folded portion of the first sheet.

11. The packaging according to claim 10, wherein said first edge of said first sheet is disposed opposite to said second edge of said package.

12. The package according to claim 10, wherein said second edge of said second sheet is spaced inwardly from said second edge of said package.

13. The package according to claim 12, wherein said first sheet is glued to said second sheet along a glue line.

14. The package according to claim 13, wherein said second set of plurality of slots are disposed between said glue line and said second edge of said package.

15. The packaging according to claim 10, wherein said second sheet is essentially transparent.

16. The packaging according to claim 10, wherein said first sheet is gusseted along said fold line and said second fold line.

17. The packaging according to claim 10, wherein said second set of plurality of slots are disposed essentially along the entire second edge of said second sheet.

18. The packaging according to claim 10, wherein said entire second sheet forming a portion of the second side of the package.

19. The packaging according to claim 10, wherein said second sheet having a third edge.

20. The packaging according to claim 19, wherein said first sheet being folded over along a third fold line forming a third folded portion, said third folded portion being connected to said second sheet, said third folded portion forms a portion of the second side of the package, said third fold line forming a third edge of said package, said third edge of second sheet being in the interior of the package between the first side and the third folded portion of the first sheet.

21. The packaging according to claim 20, further comprising an adhesive being placed on said second sheet adjacent to said third edge, a selectively removable backing paper being disposed atop said adhesive.

* * * * *